(12) United States Patent
Frantz et al.

(10) Patent No.: US 6,288,785 B1
(45) Date of Patent: Sep. 11, 2001

(54) SYSTEM FOR DETERMINING SPATIAL POSITION AND/OR ORIENTATION OF ONE OR MORE OBJECTS

(75) Inventors: Donald Dieter Frantz, Kitchener; Stephen Eldon Leis, Waterloo, both of (CA); Stefan Kirsch; Christian Schilling, both of Wuerenlingen (CH)

(73) Assignee: Northern Digital, Inc., Waterloo (CA)

( * ) Notice: Subject to any disclaimer, the term of this patent is extended or adjusted under 35 U.S.C. 154(b) by 0 days.

(21) Appl. No.: 09/428,834

(22) Filed: Oct. 28, 1999

(51) Int. Cl.$^7$ .................................................. G01B 11/14
(52) U.S. Cl. ...................... 356/614; 250/559.29; 324/226
(58) Field of Search ................................... 356/375, 376, 356/141.1, 614, 622, 623; 600/424, 429, 478, 130, 407, 427; 324/226, 207.14, 207.22; 73/510; 250/215, 559.29, 559.31

(56) References Cited

U.S. PATENT DOCUMENTS

| | | | |
|---|---|---|---|
| 5,197,476 | 3/1993 | Nowacki et al. | 128/660.03 |
| 5,295,483 | 3/1994 | Nowacki et al. | 128/660.03 |
| 5,383,454 | * 1/1995 | Bucholz | 356/375 |
| 5,622,170 | * 4/1997 | Schulz | 356/375 |
| 5,831,260 | 11/1998 | Hansen | 250/221 |
| 5,920,395 | * 7/1999 | Schulz | 356/375 |

FOREIGN PATENT DOCUMENTS

WO 00/39576  7/2000 (WO).

OTHER PUBLICATIONS

Birkfellner et al., "Concepts and Results in the Development of a Hybrid Tracking System for CAS", Lecture Notes in Computer Science: Medical Image Computing and Computer–Assisted Intervention—MICCAI '98, vol. 1496 (1998), pp. 342–351.

\* cited by examiner

Primary Examiner—Hoa Q. Pham
(74) Attorney, Agent, or Firm—Fish & Richardson P.C.

(57) ABSTRACT

A system for determining spatial position and/or orientation of one or more objects. The system includes an optical subsystem and a non-optical subsystem. The optical subsystem includes optical subsystem light sources mounted to one or more of the objects and an optical subsystem sensor adapted to detect energy from the optical subsystem light sources. The optical subsystem has an optical subsystem coordinate system in a fixed relationship with the optical subsystem sensor. The optical subsystem sensor produces position and/or orientation signals relative to the optical subsystem coordinate system in response to optical subsystem light source detected energy. The non-optical subsystem has a non-optical coordinate system and is adapted to produce position and/or orientation signals of one or more of the objects relative to the non-optical subsystem coordinate system. A coupling arrangement is provided for producing position and/or orientation signals indicative of the position and/or orientation of the selected one of the optical or non-optical subsystems relative to the coordinate system of the other one of the optical or non-optical subsystems. A processor is responsive to signals produced by the coupling arrangement and the individual subsystem sensors for determining the position and/or orientation of one or more of the objects relative to some conveniently defined coordinate system.

21 Claims, 8 Drawing Sheets

SYSTEM FOR DETERMINING SPATIAL POSITION AND/OR ORIENTATION OF ONE OR MORE OBJECTS

BACKGROUND OF THE INVENTION

This invention relates generally to systems capable of determining the spatial position and angular orientation (i.e. pose) of three-dimensional (3D) bodies or objects. More specifically, the invention relates to systems capable of tracking objects in real time within a specified volume, without regard to the objects' rigidity or visibility.

As is known in the art, a wide variety of systems have been developed that can determine the spatial position and angular orientation of objects over small time-scales, and thus track their motion in real time. These systems generally make use of specific physical phenomena, and as such, have different capabilities and limitations. One system is an optical system. Such an optical system operates on sensing of sources of radiated electromagnetic energy (e.g., light or infrared energy emitted from active markers or light or infrared energy reflected from passive markers) by sensitive arrays, such as charge coupled devices (CCD). Such optical systems can provide highly accurate spatial and angular measurements at high sampling frequencies over large operational volumes (typically room size), but require that a minimum number of the markers always be in view of the CCD sensors. This line-of-sight limitation can be partially remedied by determining the position of an obscured point from the measured positions of the visible markers with triangulation techniques. For example, markers can be affixed to instruments or probes (such as surgical probes) such that their tip points can be tracked. However, such probes must be rigid. This method cannot be applied to flexible probes such as catheters.

Another type of system is a non-optical system. Such systems include magnetic systems, mechanical systems, and ultra-sonic systems. For example, U.S. Pat. Nos. 5,197,476 and 5,295,483 to Nowacki and Horbal disclose the use of optical cameras to track the position of an ultrasonic scanner or probe, which itself detects concretions such as kidney stones within the human body. The ultrasonic scanner cannot determine the tracked object's pose, though. Magnetic systems do not suffer the line-of-sight problem inherent in optical systems; but, such systems can be severely affected by extraneous objects perturbing their magnetic fields, and are also generally less accurate. Mechanical systems use mechanical devices, such as articulating arms, and are free of line-of-sight and magnetic disturbance problems; but, such systems are considerably more expensive for a given level of accuracy. Their accuracies are subject to perturbations arising from gravitationally induced forces and torques, which limit them to the generally smaller operational volumes spanned by their range of motion. Also, they are more cumbersome than other devices since their motion is constrained by possible collisions with other objects lying within their operational volume.

As is also known in the art, optical devices can be used in conjunction with non-optical devices to overcome the optical devices' line-of-sight-limitations, but such coupling inconveniently results in the measured position data being reported in separate frames of reference, thus requiring the data to be reconciled by the user calibrating the devices to determine the necessary transformation between the two frames of reference. Birkfellner, et. al., Concepts and Results in the Development of a Hybrid Tracking System for CAS, *Lecture Notes in Computer Science: Medical Image Computing and Computer-Assisted Intervention—MICCAI'98*, Vol. 1496 (1998), pp. 342–351, describe such a system comprised of an optical tracking system and a direct current pulsed electromagnetic tracking system. They also describe procedures for calibrating and registering the magnetic system local frame of reference to the optical system frame of reference. Their system requires that the magnetic field source remain fixed after the lengthy calibration and registration procedures have been done, thus discouraging the movement of the field source to other convenient or appropriate positions as may be desired. Also, because their system reports position data from the magnetic subsystem only when the optical position data is unavailable because of obstructions in the optical system's line-of-sight, it remains essentially an optical system that is augmented by a non-optical system.

U.S. Pat. No. 5,831,260 to Hansen teaches a hybrid motion tracker having magnetic and optical sub-systems. This system is used for motion capture, using sensor assemblies (having both magnetic field sensors and optical Light Emitting diode (LED) sources) placed strategically on the person(s) being tracked to detect the motion. In normal operation, the optical sub-system provides the 3D position data, because of its inherently greater accuracy, and the magnetic sub-system provides the orientation data; if the optical sources are obscured, then the magnetic sub-system also provides the position data. Hansen's system is similar to the system described by Birkfellner, et. al, being primarily a coupling of a commercially available magnetic sub-system with a commercially available optical system, and using commercially available software to transform measurements between the subsystems (although some integration exists, such as using the optical sub-system to compensate the magnetic sub-system's degrading Signal-to-Noise ratio). Thus Hansen's system suffers the same deficiencies inherent in such systems, requiring fixed magnetic transmitters and fixed optical sensors whose fixed frames of reference must be first registered by the user by means of lengthy calibration and registration procedures, thereby precluding any easy repositioning of the sub-systems relative to one another as conveniently desired.

SUMMARY OF THE INVENTION

In accordance with the present invention, a system is provided for determining spatial position and/or orientation of one or more objects. The system includes an optical subsystem and a non-optical subsystem. The optical subsystem includes optical subsystem light sources mounted to one or more of the objects and an optical subsystem sensor adapted to detect energy from the optical subsystem light sources. The optical subsystem has an optical subsystem coordinate system in a fixed relationship with the optical subsystem sensor. The optical subsystem sensor produces position and/or orientation signals relative to the optical subsystem coordinate system in response to optical subsystem light source detected energy. The non-optical subsystem has a non-optical coordinate system and is adapted to produce position and/or orientation signals of one or more of the objects relative to the non-optical subsystem coordinate system. A coupling arrangement is provided for producing position and/or orientation signals indicative of the position and/or orientation of the selected one of the optical or non-optical subsystems relative to the coordinate system of the other one of the optical or non-optical subsystems. A processor is responsive to signals produced by the coupling arrangement and the optical subsystem and/or non-optical subsystem for determining the position and/or orientation of one or more of the objects relative to the coordinate system of the selected one of the optical or non-optical subsystems.

In one embodiment of the invention, the coupling arrangement comprises a non-optical subsystem light source having a fixed relationship to the non-optical subsystem coordinate system. The optical subsystem sensor is adapted to detect energy from the non-optical subsystem light source and produce position and/or orientation signals in response to such non-optical subsystem light source detected energy relative to the optical subsystem coordinate system. The processor is responsive to signals produced by the optical and/or non-optical subsystems for determining the position and/or orientation of one or more of the objects relative to the optical subsystem coordinate system.

In another embodiment of the invention, the coupling arrangement comprises a non-optical subsystem sensor having a fixed relationship to the optical subsystem coordinate system. The non-optical subsystem sensor is adapted to produce position and/or orientation signals of the optical subsystem light source relative to the non-optical subsystem coordinate system. The processor is responsive to signals produced by the optical subsystem sensor and/or the non-optical system sensor for determining the position and/or orientation of one or more of the objects relative to the coordinate system of the non-optical system.

With such an arrangement, a hybrid optical/non-optical tracking system is provided which operates in conjunction with a processor, that can measure and track a given 3D object's position and pose throughout the system's operational volume, both when the object is visible and when it is obscured. Furthermore, the object being tracked is not required to be a rigid body—nonrigid bodies such as catheters can be used. The ability of the present invention to track obscured nonrigid bodies is an important advantage over current optical systems. Further advantages imparted to non-optical devices that arise from their being coupled to optical devices depend on the specifics of the non-optical device.

The hybrid system also has the advantage of not requiring calibration and coordinate system alignment at the time of application. In addition, the hybrid system would still retain flexibility of arrangement—it would not be necessary to lock the subsystem components rigidly in place to maintain a fixed relative separation. For example, a non-optical subsystem could be repositioned within the optical subsystem operational volume as desired to take advantage of optimum locations or to avoid disturbances affecting its performance.

The measurement redundancy inherent in hybrid systems provides them with a further advantage over their subsystem constituents. Position tracking systems generally have accuracies that vary considerably throughout their operational volumes, being dependent on a wide variety of factors. The spatial dependence of the accuracy differs considerably between optical and non-optical devices, and typically one will be substantially more accurate than the other for a given region of space. Using measured accuracy mappings as a guide, hybrid systems can be designed that select the more accurate of the two valid measurements for a given operational subspace, or apply an appropriate weighted averaging, thus extending the overall region encompassing a desired accuracy level, compared to the equivalent regions obtained from the optical and non-optical subsystems alone.

In one embodiment of the invention, the non-optical subsystem is a magnetic tracking system and in another embodiment of the invention the non-optical subsystem is a mechanical tracking system.

BRIEF DESCRIPTION OF THE DRAWING

These and other features of the invention, as well as the invention itself, will become more readily apparent from the following detailed description when taken together with the accompanying drawings, in which.

DESCRIPTION OF THE PREFERRED EMBODIMENTS

Figure 1:
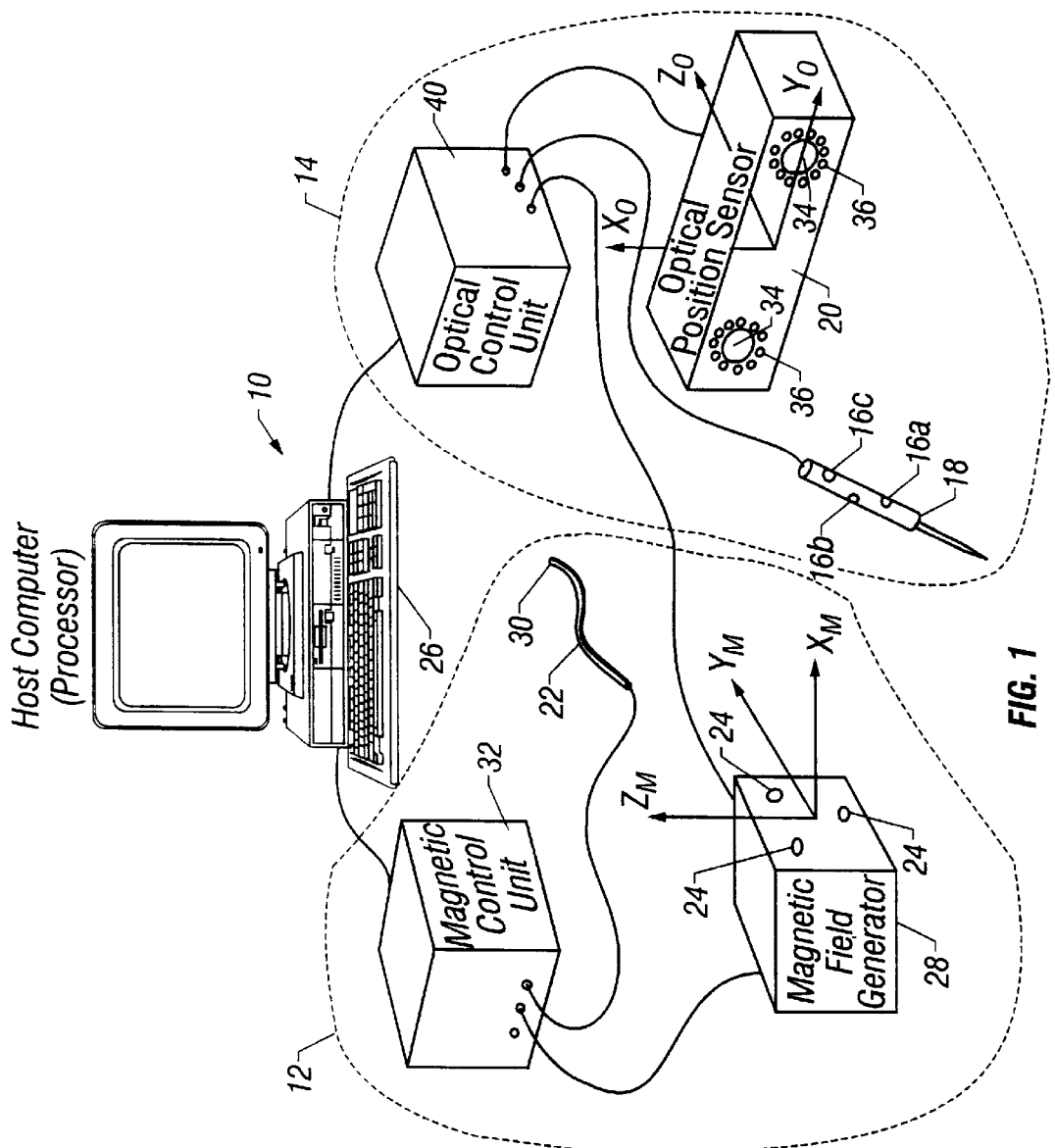
FIG. 1 is a schematic diagram of a hybrid, optical/non-optical, magnetic, system adapted to determine the spatial position and angular orientation (i.e. pose) of three-dimensional (3D) bodies or objects according to the invention.
Figure 2:
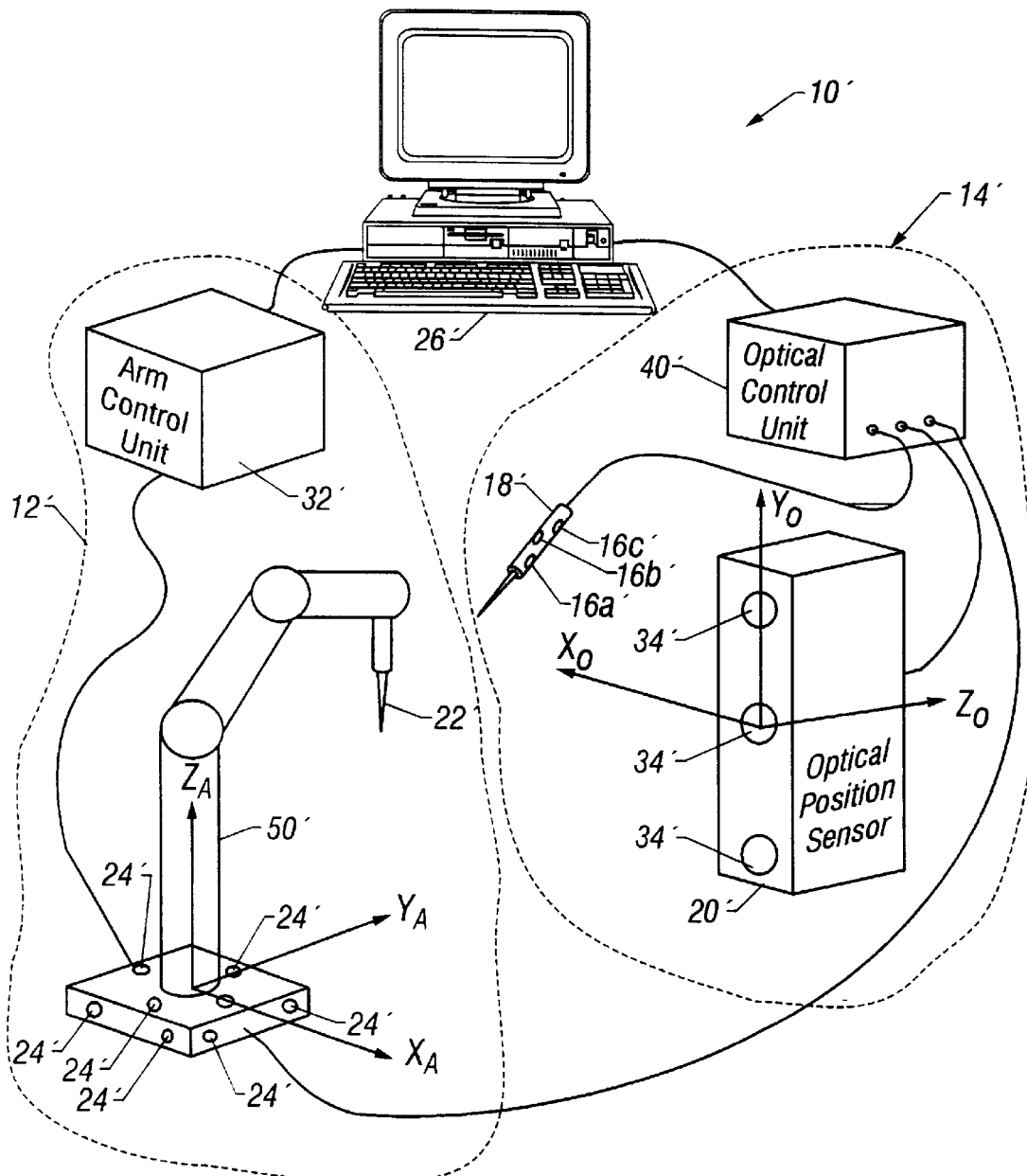

Referring now to FIGS. 1 and 2, we present two embodiments of a system for determining spatial position and/or orientation of one or more objects. In each embodiment, the system 10, 10', respectively, includes a non-optical subsystem 12, 12', respectively, and an optical 15 subsystem 14, 14', respectively. In system 10 (FIG. 1), the non-optical subsystem 12 is a magnetic tracking system and in system 10' (FIG. 2), the non-optical subsystem 12' is a mechanical tracking system. In both systems 10 and 10', the optical subsystem 14, 14', respectively, includes: an optical 20 subsystem light source, here three light sources 16a, 16b, 16c, mounted to one of the objects, here to object 18; and, a sensor 20 adapted to detected energy from the optical subsystem light sources 16a, 16b, 16c. The optical subsystem 14 has an optical subsystem coordinate system $X_O$, $Y_O$, $Z_O$ in a fixed relationship with the sensor 20. The sensor 20 produces position and/or orientation signals in response to detected energy from the optical subsystem light sources 16a, 16b, 16c relative to the optical subsystem coordinate system The non-optical subsystems 12, 12' each have a non-optical subsystem coordinate system $X_M$, $Y_M$, $Z_M$ and $X_A$, $Y_A$, $Z_A$, respectively as indicated, and are each adapted to produce position and/or orientation signals of another one of the objects 22, 22', respectively, relative to the non-optical subsystem coordinate system $X_M$, $Y_M$, $Z_M$ and $X_A$, $Y_A$, $Z_A$, respectively. The non-optical subsystems 12, 12' also include a non-optical subsystem light source, here a plurality of coupling markers 24, 24', as indicated, having a fixed relationship with the non-optical subsystem coordinate system $X_M$, $Y_M$, $Z_M$ and $X_A$, $Y_A$, $Z_A$, respectively. The sensor 20, 20' of the optical subsystem 14, 14' is adapted to detect energy from the non-optical subsystem light source 24, 24', respectively, and produce position and/or orientation signals in response to the non-optical subsystem detected energy relative to the optical subsystem coordinate system $X_O$, $Y_O$, $Z_O$. Thus, the spatial position of the non-optical coordinate system $X_M$, $Y_M$, $Z_M$, and $X_A$, $Y_A$, $Z_A$ relative to the optical subsystem coordinates $X_O$, $Y_O$, $Z_O$ are determinable by the detection, and processing, of the light energy produced by the non-optical subsystem light sources 24 by sensor 20, which sensor is in fixed relationship with the optical subsystem coordinate system $X_O$, $Y_O$, $Z_O$. A processor 26, 26' here a host computer, is responsive to signals produced by the sensor 20, 20' and determines the position and/or orientation of the objects 18, 22 and 18', 22' relative to the optical subsystem coordinate system $X_O$, $Y_O$, $Z_O$.

Thus, from the above, in FIGS. 1 and 2, the light sources 24, 24', respectively, and the sensors 34, 34' provide a coupling arrangement for producing position and/or orientation signals indicative of the position and/or orientation of the selected one of the optical or non-optical subsystems, here the non-optical coordinate systems $X_M$, $Y_M$, $Z_M$ and $X_A$, $Y_A$, $Z_A$, respectively, relative to the coordinate system of the selected one of the other one of the optical or non-optical subsystems, here the optical coordinate systems $X_O$, $Y_O$, $Z_O$.

In both embodiments, the hybrid system 10, 10' includes a single non-optical subsystem 12, 12' coupled to an optical subsystem 14. This is for illustrative purposes only, and it is understood that such hybrid systems are more general, so that hybrid systems having more than one type of non-optical subsystem could be equally well coupled to the optical subsystem in an appropriate manner.

Referring now in more detail to FIG. 1, the hybrid, optical/non-optical, tracking system 10 is shown. Here, the non-optical subsystem 12 is, as noted above, a magnetic position tracking system. The non-optical subsystem 12 is coupled to an optical subsystem 14 of the tracking system through the processor 26 and, as noted above, through the optical link between the non-optical subsystem light sources 24 and the sensor 20. Magnetic tracking systems are well known, and several variants have been developed. For illustrative purposes, here the non-optical, here magnetic, subsystem 12 of the tracking system 10 includes a magnetic field generator 28 comprised of suitably arranged electromagnetic inductive coils, not shown, that serve as the spatial magnetic reference frame (i.e., is fixed relative to the non-optical subsystem coordinate system $X_M$, $Y_M$, $Z_M$). The non-optical subsystem 12 includes small mobile inductive sensor coils 30, which are attached to the object 22 being tracked. It should be understood that other variants could be easily accommodated. The non-optical subsystem 12 also includes a magnetic system control unit 32 that is coupled to the processor 26, magnetic field generator 28 and coils 30, as indicated.

More particularly, the magnetic field generator 28, defines the magnetic coordinate reference frame ($X_M$, $Y_M$, $Z_M$) The generator 28 includes a sufficient number of coils suitably arranged to generate the source magnetic field. A small sensor coil 30 is attached to the object 22, here a flexible element (such a device could be inserted into a catheter). The position and angular orientation of the coil 30 (i.e., pose) are determined from its magnetic coupling to the source field produced by magnetic field generator 28. The magnetic system control unit 32 manages the magnetic field generator 28 and receives signals from the magnetic sensors, here the coil 30.

It is noted that the magnetic field generator 28 generates a sequence, or set, of here 6, different spatial magnetic field shapes, or distributions, each of which is sensed by the sensor coil 30. Each sequence enables a sequence of signals to be produced by the coil 30. Processing of the sequence of signals enables determination of the pose of the coil 30, and hence the pose of the object 22 to which the coil 30 is mounted relative the magnetic (non-optical) coordinate reference frame $X_M$, $Y_M$ and $Z_M$ which is in fixed relationship to the magnetic field generator 28. As noted above, a plurality of non-optical subsystem light sources 24 (i.e., emitters) is mounted to, i.e, fixed to, the magnetic field generator 28, and hence, in fixed relationship to the magnetic (non-optical)coordinate reference frame $X_M$, $Y_M$ and $Z_M$.

Similarly, optical tracking systems, such as optical subsystems 14 are well known, and several variants have been developed. Again, for illustrative purposes, here the optical subsystem 14 is an infrared system which includes the optical sensor 20, here two two-dimensional charge coupled devices (CCDs). The optical subsystem light sources 16a, 16b, 16c, (e.g., optical markers which may be passive reflectors of a source or active light emitting diodes (LEDs)) are mounted to object 18. It should be understood that other variants would be equally well suited.

More particularly, the optical subsystem 14 includes the optical position sensor 20, here comprised of two two-dimensional CCDs 34. The optical subsystem light sources 16a, 16b and 16c as well as the non-optical subsystem light sources 24 are reflective type light sources (i.e, passive markers) and here directional infrared energy source LEDs 36 are used to illuminate the passive markers 16a, 16b, 16, and 24. The infrared energy sources 36 are arranged about the CCDs 34 in an annular fashion, as indicated. The optical position sensor 20 defines (i.e, is fixed relative to) the optical coordinate reference frame, $X_O$, $Y_O$, $Z_O$. The optical position sensor 20 is coupled to an optical subsystem control unit 40 that manages the optical data collection and timing, the firing of the directional energy sources 36. It is noted that if active markers had been used for the optical subsystem light sources 16a, 16b, 16c and 24, the optical subsystem control unit 40 would manage the optical data collection and timing, the firing of the active markers 16a, 16b, 16c and 24. The unit 40 also provides as other tasks necessary for optical tracking.

The non-optical and optical (magnetic) subsystems 12, 14 are linked together through their connection to the processor 26, which synchronizes the operations of the two subsystems and manages the overall data acquisition. To provide a common reference frame for the overall system 10, the magnetic field generator 28 has a minimum of three active LED optical markers 24 shown attached to it in an arrangement well suited to define it as a rigid body to the optical subsystem 12 (it being understood that better accuracy and greater flexibility would be achieved by increasing the number of reference markers, i.e., light sources). The non-optical subsystem light sources 24 coordinates in the non-optical (magnetic) subsystem coordinate system (i.e, reference frame) $X_M$, $Y_M$ $Z_M$ would be accurately determined at the time of manufacture, when the system 10 is calibrated. Various methods can be used for the determination, such as the numerical fitting of a suitably large set of three-dimensional (3D) measurements obtained individually by the non-optical (magnetic) and optical subsystems 12, 14 within their own frames of reference, relative to some third calibration standard, or through the use of hybrid tools comprised of optical markers and magnetic sensors combined in a suitable arrangement.

With the positions of the non-optical light sources 24 (i.e., the magnetic field reference markers) known relative to the non-optical coordinate system $X_M$, $Y_M$, $Z_M$, the positions and poses of the object 22 being tracked by the overall hybrid system 10 can be reported in a common reference frame, here the common reference being the optical subsystem coordinate system $X_O$, $Y_O$, $Z_O$, fixed relative to the optical position sensor 20.

It should be understood that the non-optical coordinate reference $X_M$, $Y_M$, $Z_M$ can also be coupled to the optical reference frame $X_O$, $Y_O$, $Z_O$ by having a magnetic sensor 30a fixed to the optical position sensor 20 relative to the non-optical coordinate reference $X_M$, $Y_M$, $Z_M$.

If the magnetic subsystem reference frame $X_M$, $Y_M$, $Z_M$ is chosen as the common reference frame, then the transformation TOM will convert measurements in the optical subsystem coordinate system $X_O$, $Y_O$, $Z_O$ to their equivalent non-optical subsystem coordinate system $X_M$, $Y_M$, $Z_M$. Such transformation methods are well known, and are completely general; the common reference frame need not be limited to either of the subsystem (reference frames) $X_O$, $Y_O$, $Z_O$ or $X_M$, $Y_M$, $Z_M$, but can be any convenient arbitrary frame. The transformations are done on the processor 26 in this implementation, but this is not required. The magnetic and optical system control units 32, 40 could also be linked together to exchange data directly prior to position determinations and transformations. Either way, the combined data from the two subsystems 12, 14 provides advantages otherwise not available. For example, the optically measured position can be used to initialize the magnetic position determination algorithm, decreasing the calculation time considerably.

The optical tracking of the magnetic field generator 28 with non-optical light sources 24 in this embodiment has the advantage of allowing the magnetic field generator 28 to be optimally repositioned with respect to the tracking volume to avoid interference from magnetic and conductive objects, or to obtain the best performance of the magnetic subsystem. Note that the tracking procedure need not be interrupted while the position of the magnetic field generator 28 is changed.

Figure 1A:
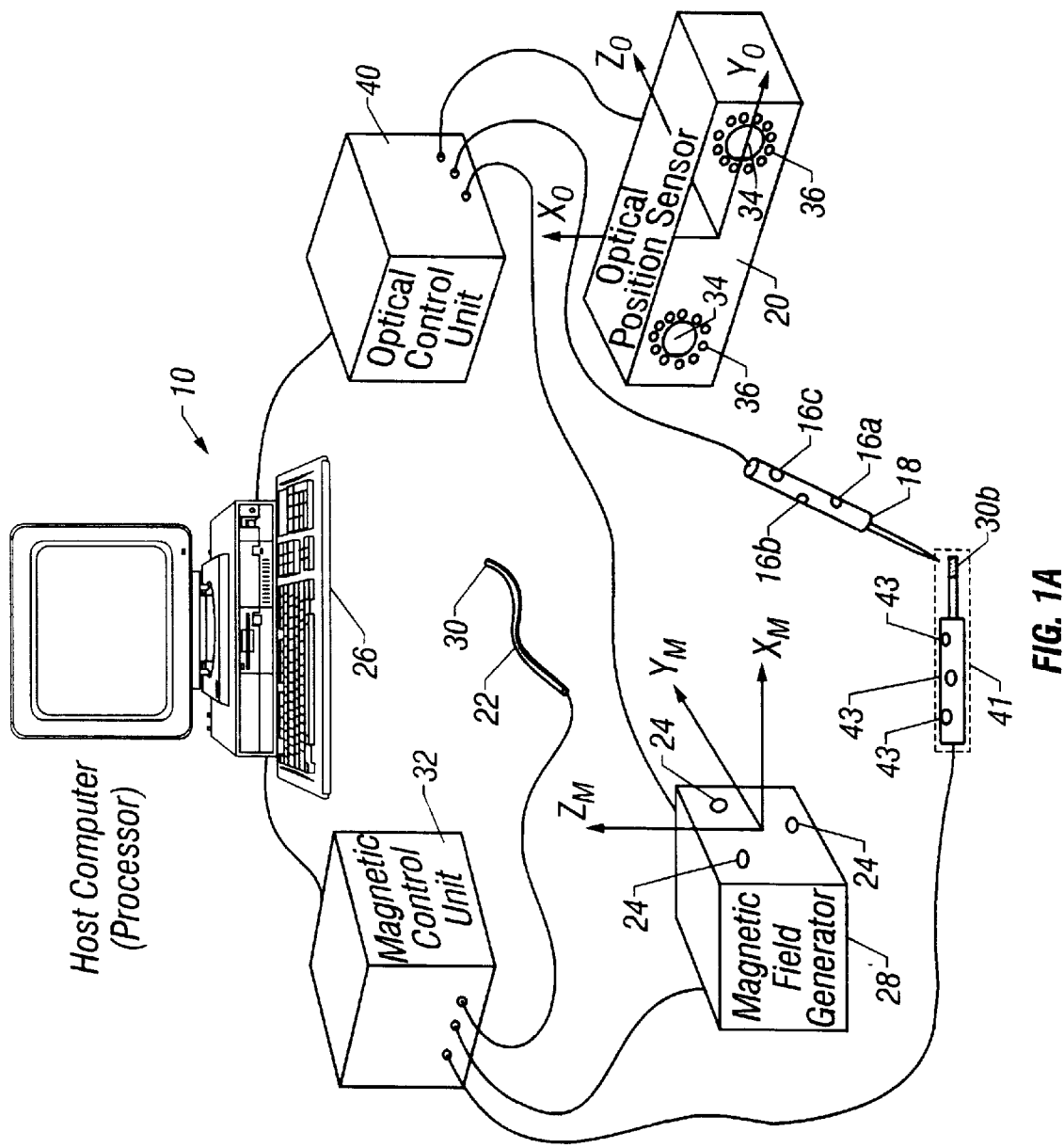
FIG. 1A is a schematic diagram of an alternative embodiment of a hybrid, optical/non-optical, magnetic, system adapted to determine the spatial position and angular orientation (i.e. pose) of three-dimensional (3D) bodies or objects according to the invention.

Referring now to FIG. 1A, a hybrid optical-magnetic probe 41 is shown in the system 10 of FIG. 1, (where like elements are designated by the same numerical designation as used in FIG. 1). Such probe 41 has a magnetic sensor, here a coil 30b, located at its end position, as well as three visible active optical subsystem light sources 43 detectable by sensor 20 (FIG. 1) that can be used to define the probe as a rigid body, and thus simultaneously track the end position with the magnetic sensor 30b. Such a probe 41 can be used as a reference, for example, to detect possible magnetic disturbances that could affect the magnetic measurements.

Although this embodiment shows only a single magnetic field generator 28, greater flexibility and extension could be achieved by using multiple field generators, each separately tracked with its own set of non-optical subsystem light sources 24 (FIG. 1), i.e., optical markers. The easiest method would be to optically track individual field generators 28, which could be conveniently located as appropriate throughout the optical subsystem 12 operational volume, thus greatly enhancing the magnetic subsystem operational volume. This would be equivalent to a customizable magnetic field generator that could be optimally arranged to best accommodate the constraints inherent to a specific measurement situation. For example, in a surgical application, the coils could be appropriately arranged over the patient's body to greatly extend the operational range of a catheter containing the magnetic sensor.

Figure 1B:
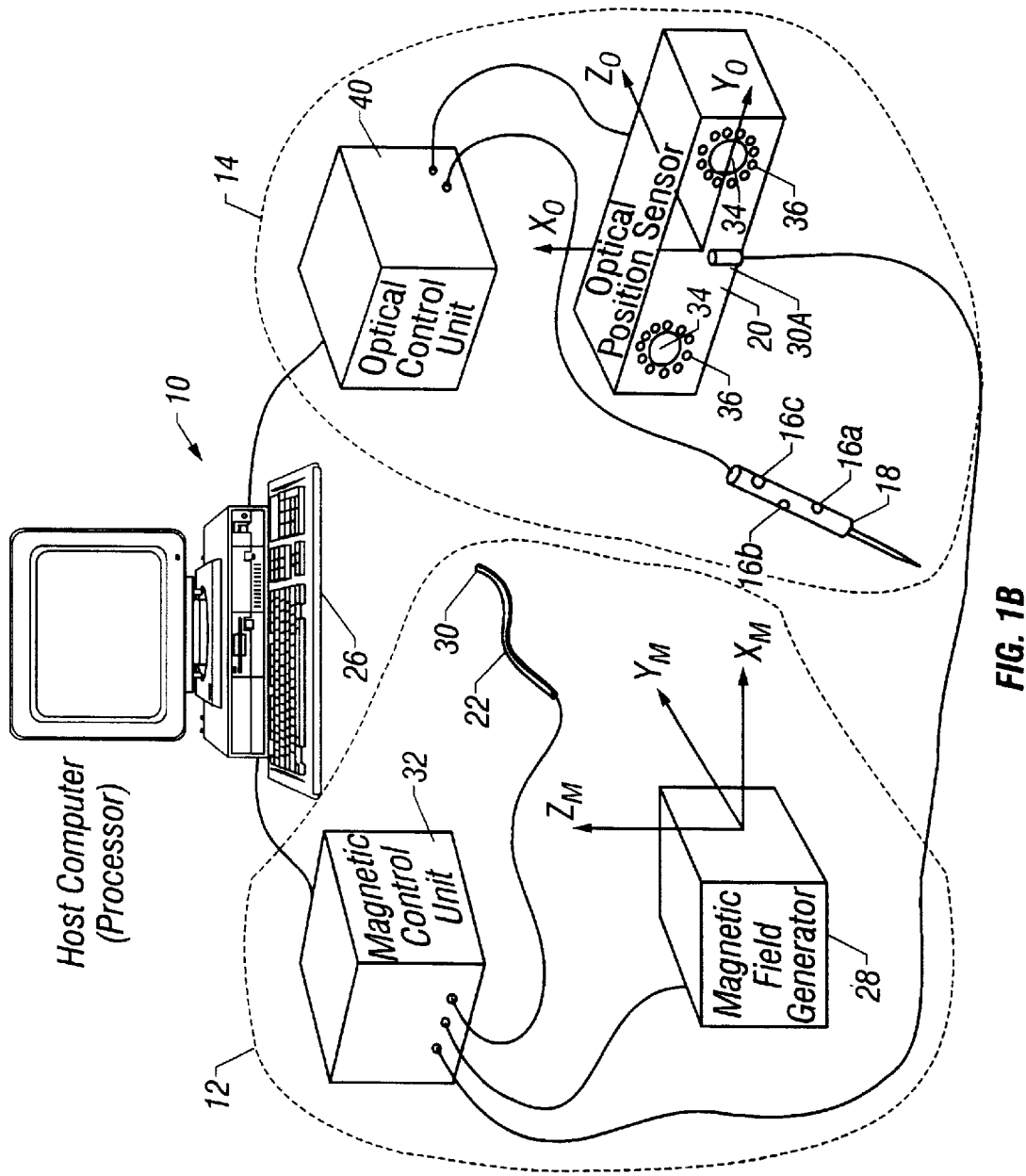
FIG. 1B is a schematic diagram of another alternative embodiment of a hybrid, optical/non-optical, magnetic, system adapted to determine the spatial position and angular orientation (i.e. pose) of three-dimensional (3D) bodies or objects according to the invention; and, FIG. 2 is a schematic diagram of a hybrid, optical/non-optical system adapted to determine the spatial position and angular orientation (i.e. pose) of three-dimensional (3D) bodies or objects according to another embodiment of the invention.

As noted above, the coupling between the optical and magnetic subsystems 14, 12 (FIG. 1) in this embodiment through the use of non-optical subsystem light sources 24 affixed to the magnetic field generator 28 could be augmented by also affixing magnetic sensors such as coil 30a onto the optical sensor 20 itself, as shown in FIG. 1B (where like elements are designated by the same numerical designation as used in FIG. 1) thereby allowing the alignment of the individual non-optical (magnetic) and optical subsystem coordinate systems ($X_M$, $Y_M$, $Z_M$ and $X_O$, $Y_O$, $Z_O$, respectively, even when no direct line of sight exists between the two. This would require that the optical sensor 20 be housed in a properly shielded casing made from materials that would not interfere with the magnetic fields, or that any influences from electrically conducting or magnetic materials be compensated by other means.

Thus, from the above, in FIG. 1B, the coil 30a has a fixed relationship to the optical subsystem coordinate system and is adapted to produce position and/or orientation signals of the optical subsystem sensor 20 relative to the non-optical subsystem coordinate system. Thus, here the coil 30a provides a coupling arrangement for producing position and/or orientation signals indicative of the position and/or orientation of the selected one of the optical or non-optical subsystems, here the optical coordinate system $X_O$, $Y_O$, $Z_O$ relative to the coordinate system of the other one of the optical or non-optical subsystems, here the non-optical coordinate systems $X_M$, $Y_M$, $Z_M$.

Referring now to FIG. 2, the hybrid optical/non-optical tracking system 10' is shown. It is noted that like elements used herein and used in the system 10 of FIG. 1 are designated with the same numerical designation. As noted above, the non-optical subsystem 12' is a mechanical tracking subsystem, here an articulating arm 50'. The arm 50' is coupled to the optical subsystem 14' of the tracking system 10' though the non-optical subsystem light sources 24' affixed to the arm 50' and detection of light from the sources 24' by the optical position sensor 20'. Mechanical articulating arm systems are well known, and several variants have been developed. Smaller arms can have better accuracy than optical systems, but are limited to operational volumes much smaller than typical optical system operational volumes. Here, again, the optical subsystem 14' operates in the infrared region, this time consisting of an optical sensor 20' comprised of three one-dimensional CCDs 34; other variants would be equally well suited. Unlike the magnetic/optical embodiment already considered in connection with FIG. 1, this embodiment does not handle non-rigid bodies because of the fundamental limitations inherent to articulating arms, but it does provide an example of the enhancement brought about to a non-optical device by coupling it to an appropriate optical device.

Thus, as shown in FIG. 2, the articulating arm 50' defines the non-optical (arm) subsystem coordinate system (reference frame) $X_A$, $Y_A$, $Z_A$. The arm 50' includes, as noted above, a plurality of mechanically linked rigid segments, stiffly connected, that can be rotated and moved about such that the end-effector 22' can be positioned as desired within the arm's operational volume of motion. The positions and orientations of each segment are accurately determined and combined to give the end-effector 22' position relative to the arm's local reference frame (i.e., the non-optical subsystem coordinate system $X_A$, $Y_A$, $Z_A$). The arm's control unit 32' manages the data acquisition from the arm and interfaces the unit to the processor 26'.

The optical subsystem 14' includes a position sensor 20' comprised of three one-dimensional CCDs 34'. The position sensor 20' defines the optical coordinate reference frame ($X_O$, $Y_O$, $Z_O$). An example rigid probe 18' with three visible active LED markers 16'a, 16'b, 16'c is coupled to the control unit 40'. The optical position sensor 20' is attached to control unit 40' that manages the optical data collection and timing, the firing of the active marker LEDs, as well as other tasks necessary for optical tracking.

The non-optical (mechanical) and optical subsystems 12' 14' are linked together through their connection to the processor 26', which synchronizes the operations of the two subsystems and manages the overall data acquisition, and through the detection of light from the non-optical subsystem light sources 24' by the optical position sensor 20', in order to provide a common reference frame for the overall system 10', here the optical subsystem coordinate system $X_O$, $Y_O$, $Z_O$ fixed relative to the sensor 20'. More particularly, the articulating arm 50' has a plurality of active LED optical markers(i.e., the non-optical subsystem light sources 24' attached to it in an arrangement well suited to define it as a rigid body to the optical subsystem 14'. The processor 26' handles the transformations from the arm's frame of reference (i.e, the non-optical subsystem coordinate system $X_A$, $Y_A$, $Z_A$) to the optical subsystem's 14' frame of reference (i.e., the optical subsystem coordinate system $X_O$, $Y_O$, $Z_O$). Thus the arm 50' can be relocated anywhere within the optical subsystem's 14' operational volume, thereby greatly extending the arm's effective operational volume. The position of the non-optical subsystem light sources 24' relative to the non-optical subsystem coordinate system $X_A$, $Y_A$, $Z_A$ would be accurately determined at the time of manufacture, when the system 10' is calibrated.

With the positions of the articulating arm reference markers (i.e., non-optical subsystem light sources 24') known, the position of the arm end-effector 22' can be reported in a common reference frame, here the optical subsystem coordinate system $X_O$, $Y_O$, $Z_O$. Transformation methods for converting the local arm coordinates to the optical subsystem's frame of reference (i.e., the optical subsystem coordinate system $X_O$, $Y_O$, $Z_O$) are well known, and are completely general; again, the common reference frame need not be limited to either of the subsystem reference frames, but can be any convenient arbitrary frame. The transformations are done on the processor 26' in this implementation, but this is not required if the two subsystem control units 32' 40' are connected so that they can directly 1s exchange data.

Figure 3:
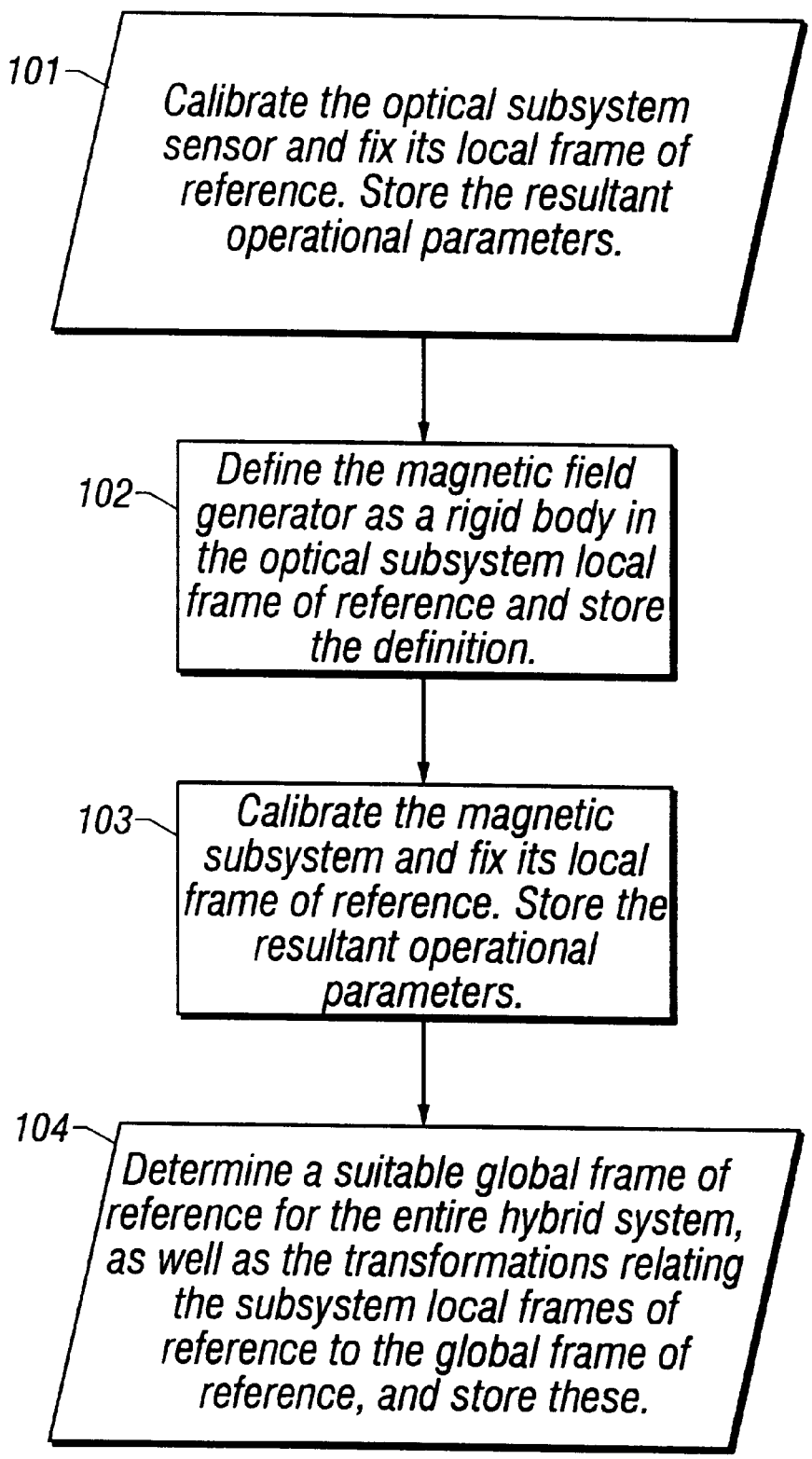
FIG. 3 is a process flow diagram describing the calibration of the hybrid, optical/non-optical system of FIG. 1A.

An example factory calibration of a magnetic/optical hybrid system is illustrated in the flow diagram, FIG. 3. There is much flexibility in this process, in part because of the variety of other position measurement devices available for use as standards, and thus many other variations of the process described in FIG. 3 would be well suited to the task. It is necessary that the standard device be substantially more accurate than either of the two subsystem devices over their respective operational volumes; in this example, a coordinate measuring machine (CMM) is assumed to be the standard. As stated in FIG. 3, Step 101, the optical subsystem is calibrated first. This is well known in the art and typically involves the accurate positioning of optical markers in some suitable grid-like fashion throughout the operational volume of the optical sensor 20 and measuring the sensor CCD data. The sensor data and CMM position data are then used to determine the sensor's operational parameters and local frame of reference ($X_O$, $Y_O$, $Z_O$), which are subsequently used to convert the sensor data to their corresponding 3D position data during the sensor's normal operation. After the sensor parameters have been determined, the sensor data collected during the calibration can be converted to 3D positions, and compared to the standard 3D positions. The differences can be used to form a mapping of the sensor's spatial error distribution, which can be recorded for subsequent use in the hybrid system 3D position determination algorithms.

As stated in FIG. 3, Step 102, the magnetic field generator 28 is then defined as a rigid body in the optical subsystem reference frame ($X_O$, $Y_O$, $Z_O$). Again, this is a well known practice in the art, and typically involves measuring the 3D positions of the reference LED markers 24 affixed to the generator 28 relative to one another. The marker positions can be subsequently used to define a local coordinate system whose origin and orientation can be conveniently located within the rigid body. In this case, aligning the local rigid-body coordinate system with the local magnetic subsystem frame of reference ($X_M$, $Y_M$, $Z_M$) after it is determined is preferred.

The magnetic subsystem is calibrated next, Step 103. The magnetic field generator 28 and the optical sensor 20 are positioned such that each of their operational volumes lie within the CMM operational volume and such that there is a clear line of sight between the field generator reference markers 24 and the optical sensor 20. The position and pose of the field generator 28 is measured by the optical sensor 20 and recorded. A hybrid optical/magnetic sensing tool 41 having the magnetic sensor defined as a virtual marker, so that the optical and magnetic measurements are coincident, is affixed to the CMM end-effector and accurately positioned in a suitable grid-like manner throughout the magnetic subsystem operational volume, while the magnetic sensor data and optical sensor data corresponding to each magnetic sensor position are recorded. The magnetic sensor data and the CMM 3D position data are then used to determine the magnetic subsystem's operational parameters and local frame of reference, ($X_M$, $Y_M$, $Z_M$), which are subsequently used to convert the magnetic sensor data to their corresponding 3D position data during normal operation. Similar to the optical subsystem calibration, after the magnetic subsystem parameters have been determined, the magnetic sensor data collected during the calibration can be converted to 3D positions and compared to the standard 3D positions so that their differences can be used to form a mapping of the magnetic subsystem's spatial error distribution. Note that although we have used a CMM to calibrate both subsystems, the optical subsystem itself could have been used instead to calibrate the magnetic subsystem, provided it were sufficiently more accurate than the magnetic subsystem.

The optical and magnetic 3D data corresponding to the hybrid tool positions, together with the field generator location and rigid-body data defined by the reference markers 24, can be used to calculate the required transformations between the optical subsystem and magnetic subsystem local frames of reference, ($X_O$, $Y_O$, $Z_O$) and ($X_M$, $Y_M$, $Z_M$), respectively. The hybrid system global frame of reference can then be determined in Step 104. The calculations used to determine these transformations are well known in the art.

These transformations can be stored on either the system control units 32 and 40, or the host computer 26, depending on the system design, and updated as required whenever the field generator 28 or sensor device 20 is repositioned.

Figure 4A:
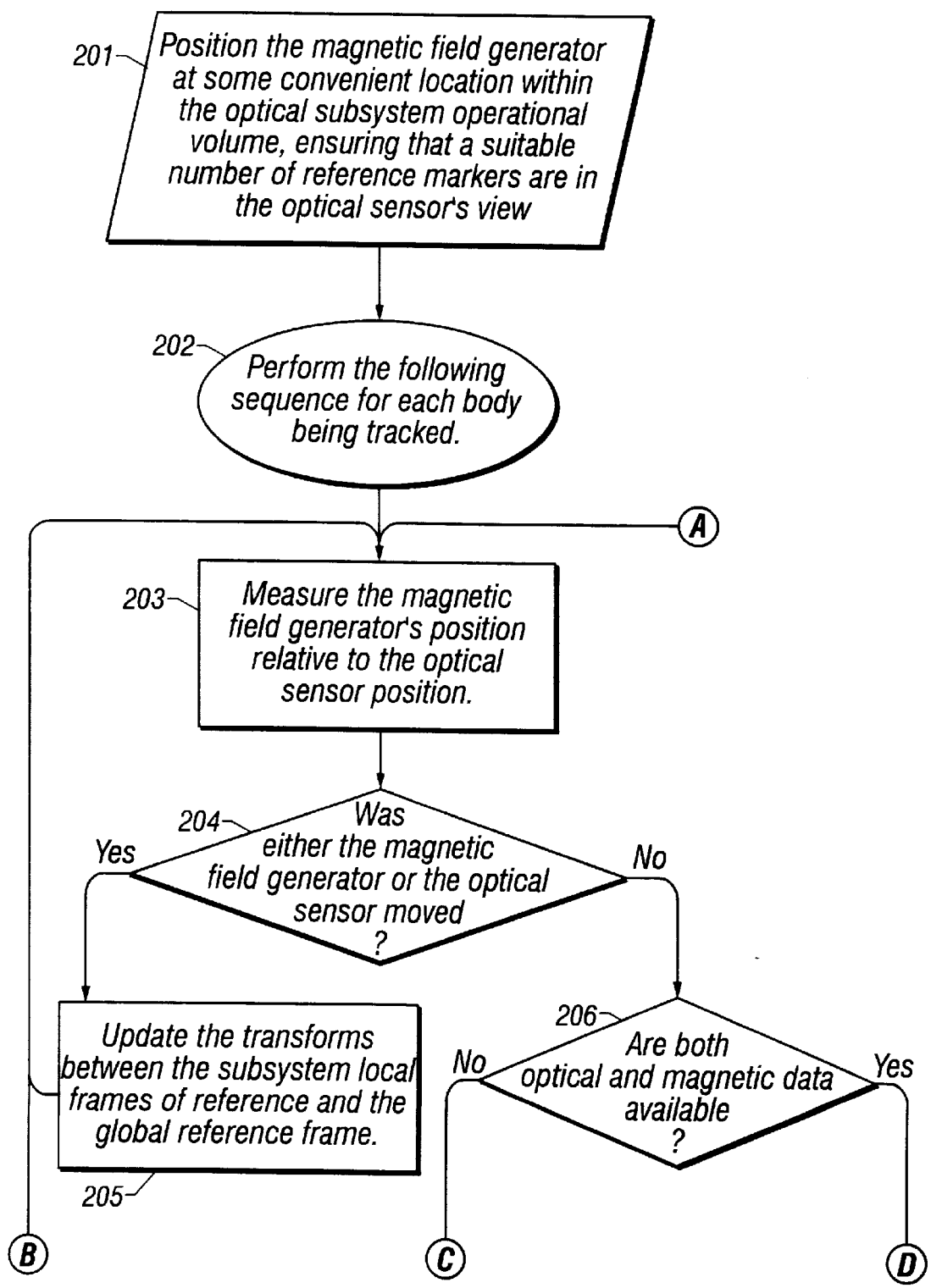
FIGS. 4A, 4B, and 4C together depict is a process flow diagram describing the basic operation of the hybrid, optical/magnetic system of FIG. 1A.
Figure 4B:
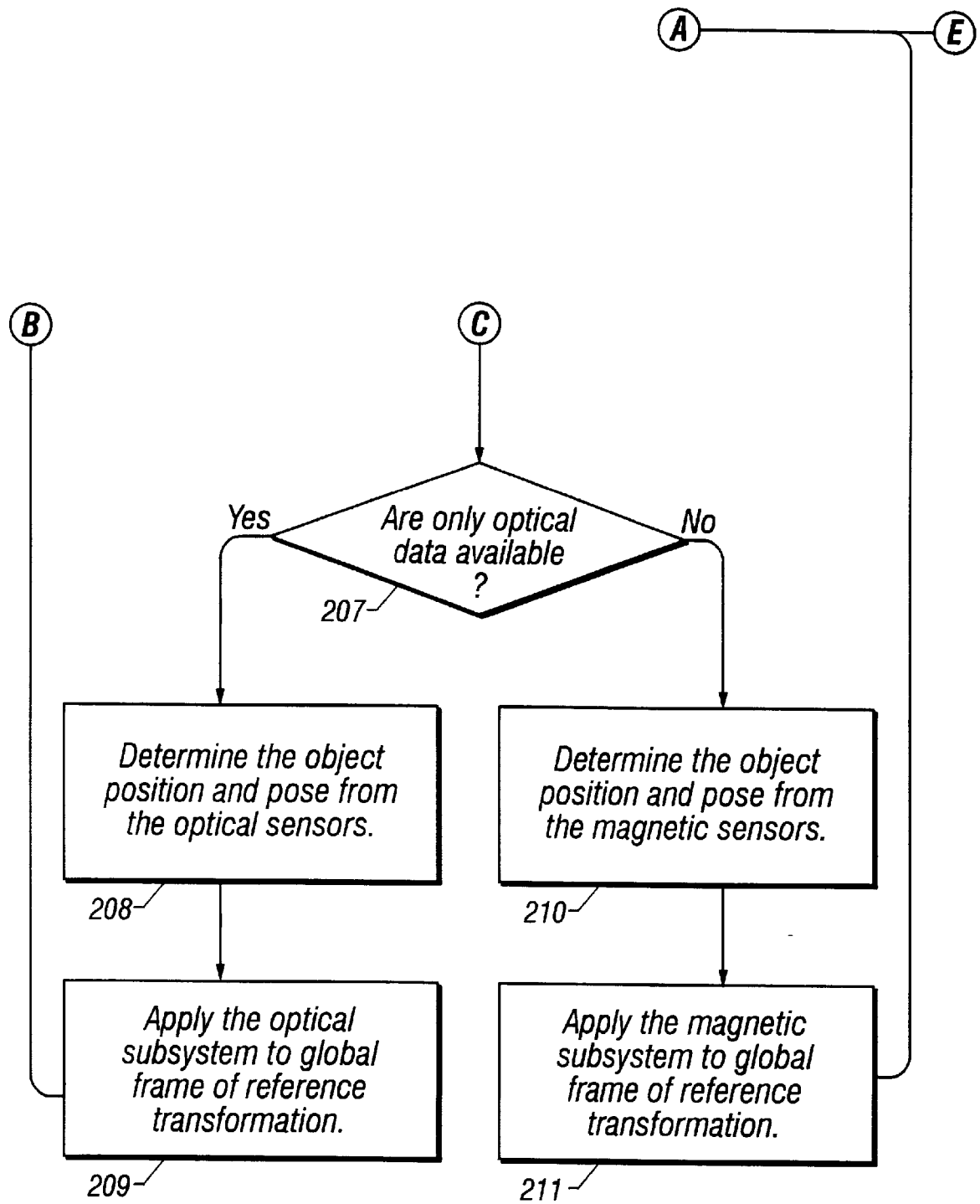
Figure 4C:
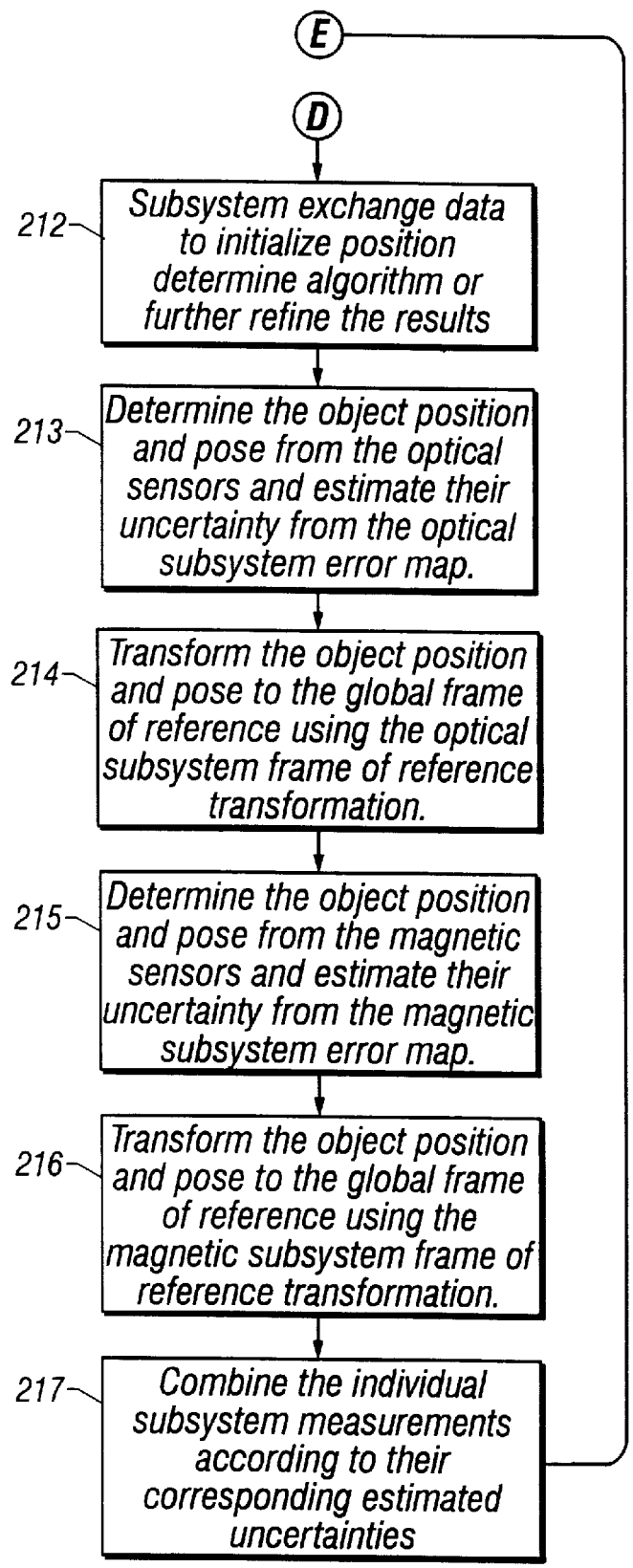

An example measurement process corresponding to the hybrid, optical/magnetic system described in FIG. 1a is illustrated in the flow diagram, FIGS. 4A, 4B and 4C. In this example, a number of different objects are tracked by the hybrid system. Some of these objects contain both optical markers and magnetic sensors (such as the hybrid tool 41), while other objects contain only optical markers (such as the optical probe 18) or magnetic sensors (such as the magnetic sensor 30). As described in FIG. 4A, Step 201, the magnetic field generator 28 is conveniently positioned within the operational volume of the optical sensor 20 such that the reference marker LEDs 24 are visible to the optical sensor.

The measurement process for each object being tracked begins in FIG. 4, Steps 202, 203 with the optical sensor 20 determining the position of the magnetic field generator 28 and thus the position of the magnetic subsystem local frame of reference $(X_M, Y_M, Z_M)$ relative to the optical subsystem local frame of reference $(X_O, Y_O, X_O)$. If the field generator 28 has been moved relative to the optical sensor, the transforms between the subsystem local frames of reference and the global frame of reference are all updated to reflect the new positions and orientations (FIG. 4A, Steps 204 and 205), otherwise, the determination of the object's position and pose begins (Step 206).

The system first determines whether optical or magnetic data, or both types, are available. If only one type of data is present, either because the object being tracked has only one class of transducer (such as the optical probe 18 or the magnetic sensor 30), or because one type of data is invalid (such as the optical markers 43 on the hybrid tool 41 being obscured, or its magnetic sensor 30b being out of range), or simply because one type of data is unavailable (the optical and magnetic data collection frequencies could differ), then the measurement process branches to the appropriate subsystem (FIG. 4B, Step 207). For optical data, the optical subsystem determines the object's position and pose from the optical sensors in the local frame of reference and then transforms the data to the global frame of reference (FIG. 4A, Steps 208 and 209), while for magnetic data, the magnetic subsystem determines the object's position and pose from the magnetic sensors in the subsystem's local frame of is reference and then transforms the data to the global frame of reference (FIG. 4, Steps 210 and 211).

If both types of data are available, then the object's position and pose are determined by each subsystem in its local frame of reference and transformed to the global frame of reference in the usual manner, except that the subsystems can also exchange data between each other to assist the position and orientation calculations by initializing their determination algorithms, or to further refine calculated positions and orientations (FIG. 4C, Steps 212 to 216). Also, the uncertainties for each measurement are estimated from the subsystem error maps that were determined during factory calibration. The redundant measurements are then combined according to their estimated uncertainties to give a final position and pose, which is reported to the user (FIG. 4C, Step 217). Various methods of combining the redundant measurements are possible, including simply selecting the more accurate one, or weighted averaging according to uncertainty inverses. More sophisticated algorithms could also be used to recognize and discriminate anomalous measurements by thresholding differences between the subsystem measurements according to their respective uncertainties, so that, for example, a magnetic measurement perturbed by the presence of a metal object near the sensors would be recognized by its significant difference from the optical measurement and thus ignored.

In view of the foregoing description of the two embodiments described above, it will now be recognized that, a hybrid optical/non-optical system 10, 10' is provided for tracking the positions and orientations of three-dimensional (3D) objects, both rigid and nonrigid, in space. The optical subsystem 14, 14' of the systems 10, 10' have some appropriate form of light sensors (typically, three or more one-dimensional charge-coupled devices (CCDs), or two or more two-dimensional CCDs), a plurality of optical subsystem light sources (typically, active light emitting diode (LED) markers, or passive reflecting markers), and an electronic system control unit to manage the various operational aspects of the subsystem. The hybrid system includes an appropriate non-optical subsystem, or subsystems which are complementary to the optical subsystem in the sense that it is not subject to line-of-sight limitations. The non-optical subsystem includes, but is not limited to, magnetic tracking devices, articulating mechanical arms, and optical fiber devices. The non-optical subsystem may include a plurality of at least three non-optical subsystem light sources properly affixed in known locations on some appropriate part of the device so as to form a rigid body that allows for coordinate transformations between the optical and non-optical subsystem coordinate reference frames. The hybrid system includes a processor interface and data management program that synchronizes the operation of the optical and non-optical subsystems, performs the required subsystem measurement coordinate transformations to the hybrid-system's reference frame, and properly selects or determines the best measurement in the case of redundant measurements from the two or more subsystems.

Further, it is noted that the coupling between the optical and non-optical subsystems is general such that the subsystems can be repositioned relative to one another to better take advantage of subsystem-specific optimum locations and to lessen the detrimental effects of subsystem-specific disturbances. Further, the reference optical markers affixed to the non-optical subsystem(s) are accurately determined at time of manufacture, precluding the requirement of calibration and subsystem coordinate alignment being done at the time of application. The methods used for the said calibration depend on the specifics of the optical and non-optical subsystems. These include, but are not limited to, the numerical fitting of large sets of 3D position measurements obtained individually with the subsystems within their own frames of reference, relative to some calibration standard, and the use of hybrid optical/non-optical calibration tools.

Further, the individual subsystem control units responsible for determining object positions and orientations (within the subsystem local frame of reference) through the use of appropriate calculational procedures are directly connected together to exchange the said position and orientation values in real-time so that transformations to a common hybrid system global frame of reference can be performed. In lieu of such a direct connection between the subsystems, the said transformations shall be calculated and applied on the processor. The optical and non-optical subsystems have their 3D positional and orientational accuracies mapped as functions of their spatial locations at the time of manufacture to provide the basis for appropriate selection or determination of the optimum measurement values in case of redundant measurements from the subsystems.

With regard to the magnetic non-optical subsystem, it is noted that the magnetic subsystem includes one or more field generators and a number of magnetic sensors, one or more of which are affixed to the optical subsystem in such a manner as to allow the determination of the optical subsystem's frame of reference within the magnetic subsystem's frame of reference, thereby allowing the alignment of the two said frames of reference even when there is no line of sight between them.

With regard to the magnetic non-optical subsystem, it is also noted that the magnetic subsystem can comprise a number of separate, individual electromagnetic inductive field generator coils, each having at least three optical markers affixed to it in such a manner as to define it as a rigid body within the said optical subsystem's frame of reference, such that the individual coils can be placed anywhere within the said optical subsystem operational volume and tracked by the optical sensors, thereby allowing the magnetic subsystem to be optimally adapted to track magnetic sensors over larger, more irregular sub-volume shapes and forms, than would be possible by a fixed array of generator coils localized within a single field generator unit.

With further regard to the magnetic non-optical subsystem, it should also be understood by one skilled in the art that the magnetic sub-system need not be restricted to an active field generator with passive magnetic sensors, but that its complement, a magnetic sub-system comprised of active magnetic "sensors" generating the fields, which are then detected by the passive "field generator" within its frame of reference, would also be suitable.

Other embodiments are within the spirit and scope of the appended claims.

What is claimed is:

1. A system for determining the location of one or more objects, comprising:
   a first subsystem having a first set of sensors and a first coordinate system, said first set of sensors producing a first data signal indicative of the position and orientation of said one or more objects within said first coordinate system, wherein said first subsystem produces a first subsystem location signal, responsive to said first data signal, which is indicative of the location of said one or more objects within said first coordinate system, wherein said first data signal is also provided to a second subsystem;
   said second subsystem having a second set of sensors and a second coordinate system, said second set of sensors producing a second data signal indicative of the position and orientation of said one or more objects within said second coordinate system, wherein said second subsystem produces a second subsystem location signal, responsive to said second data signal, which is indicative of the location of said one or more objects within said second coordinate system, wherein said second data signal is also provided to said first subsystem;
   a coupling arrangement for producing a coupling location signal indicative of the location of said first subsystem within said second coordinate system of said second subsystem; and
   a processor responsive to said coupling location signal and at least one of said subsystem location signals for locating said one or more objects within said first coordinate system of said first subsystem;
   wherein said first subsystem uses said second data signal to enhance the robustness and accuracy of said first subsystem location signal;
   wherein said second subsystem uses said first data signal to enhance the robustness and accuracy of said second subsystem location signal.

2. The system of claim 1 wherein said first subsystem is an optical subsystem and said second subsystem is a magnetic subsystem.

3. The system of claim 2 wherein said optical subsystem comprises:
   at least one optical light source positioned proximate said one or more objects; and
   an optical sensor configured to detect energy from said at least one optical light source;
   wherein said optical sensor is in a fixed spatial relationship with said first coordinate system;
   wherein said optical sensor produces said first data signal representative of energy detected from said at least one optical light source.

4. The system of claim 3 wherein said magnetic subsystem comprises:
   a magnetic transmitter; and at least one magnetic sensor positioned proximate said one or more objects, said at least one magnetic sensor being configured to detect energy from said magnetic transmitter;
   wherein said magnetic transmitter is in a fixed spatial relationship with said second coordinate system;
   wherein said at least one magnetic sensor produces said second data signal representative of energy detected from said magnetic transmitter.

5. The system of claim 4 wherein said coupling arrangement comprises:
   a magnetic subsystem sensor in a fixed relationship with said first coordinate system;
   wherein said magnetic subsystem sensor produces said coupling location signal representative of energy detected from said magnetic transmitter.

6. The system of claim 1 wherein said first subsystem is a magnetic subsystem and said second subsystem is an optical subsystem.

7. The system of claim 6 wherein said magnetic subsystem comprises:
   a magnetic transmitter; and
   at least one magnetic sensor positioned proximate said one or more objects, said at least one magnetic sensor being configured to detect energy from said magnetic transmitter;
   wherein said magnetic transmitter is in a fixed spatial relationship with said first coordinate system;
   wherein said at least one magnetic sensor produces said first data signal representative of energy detected from said magnetic transmitter.

8. The system of claim 7 wherein said optical subsystem comprises:
   at least one optical light source positioned proximate said one or more objects; and
   an optical sensor configured to detect energy from said at least one optical light source;
   wherein said optical sensor is in a fixed spatial relationship with said second coordinate system;
   wherein said optical sensor produces said second data signal representative of energy detected from said at least one optical light source.

9. The system of claim 8 wherein said coupling arrangement comprises:
   a optical subsystem light source in a fixed relationship with said first coordinate system;
   wherein said optical sensor is further configured to detect energy from said optical subsystem light source;
   wherein said optical sensor produces said coupling location signal representative of energy detected from said optical subsystem light source.

10. The system of claim 1 wherein said subsystem location signals each include a position signal indicative of the position of said one or more objects within said first and second coordinate systems.

11. The system of claim 1 wherein said subsystem location signals each include an orientation signal indicative of the orientation of said one or more objects within said first and second coordinate systems.

12. A system for determining the location of one or more objects, comprising:
- a first subsystem having a first set of sensors and a first coordinate system, said first set of sensors producing a first data signal indicative of the position and orientation of said one or more objects within said first coordinate system, wherein said first subsystem produces a first subsystem location signal, responsive to said first data signal, which is indicative of the location of said one or more objects within said first coordinate system, wherein said first data signal is also provided to a second subsystem;
- said second subsystem having a second set of sensors and a second coordinate system, said second set of sensors producing a second data signal indicative of the position and orientation of said one or more objects within said second coordinate system, wherein said second subsystem produces a second subsystem location signal, responsive to said second data signal, which is indicative of the location of said one or more objects within said second coordinate system, wherein said second data signal is also provided to said first subsystem;
- a coupling arrangement for producing a coupling location signal indicative of the location of said first subsystem within said second coordinate system of said second subsystem; and
- a processor responsive to said coupling location signal and at least one of said subsystem location signals for locating said one or more objects within said second coordinate system of said second subsystem;
- wherein said first subsystem uses said second data signal to enhance the robustness and accuracy of said first subsystem location signal;
- wherein said second subsystem uses said first data signal to enhance the robustness and accuracy of said second subsystem location signal.

13. The system of claim 12 wherein said first subsystem is an optical subsystem and said second subsystem is a magnetic subsystem.

14. The system of claim 13 wherein said optical subsystem comprises:
- at least one optical light source positioned proximate said one or more objects; and
- an optical sensor configured to detect energy from said at least one optical light source;
- wherein said optical sensor is in a fixed spatial relationship with said first coordinate system;
- wherein said optical sensor produces said first data signal representative of energy detected from said at least one optical light source.

15. The system of claim 14 wherein said magnetic subsystem comprises:
- a magnetic transmitter; and
- at least one magnetic sensor positioned proximate said one or more objects, said at least one magnetic sensor being configured to detect energy from said magnetic transmitter;
- wherein said magnetic transmitter is in a fixed spatial relationship with said second coordinate system;
- wherein said at least one magnetic sensor produces said second data signal representative of energy detected from said magnetic transmitter.

16. The system of claim 15 wherein said coupling arrangement comprises:
- a magnetic subsystem sensor in a fixed relationship with said first coordinate system;
- wherein said magnetic subsystem sensor produces said coupling location signal representative of energy detected from said magnetic transmitter.

17. The system of claim 12 wherein said first subsystem is a magnetic subsystem and said second subsystem is an optical subsystem.

18. The system of claim 17 wherein said magnetic subsystem comprises:
- a magnetic transmitter; and
- at least one magnetic sensor positioned proximate said one or more objects, said at least one magnetic sensor being configured to detect energy from said magnetic transmitter;
- wherein said magnetic transmitter is in a fixed spatial relationship with said first coordinate system;
- wherein said at least one magnetic sensor produces said first data signal representative of energy detected from said magnetic transmitter.

19. The system of claim 18 wherein said optical subsystem comprises:
- at least one optical light source positioned proximate said one or more objects; and
- an optical sensor configured to detect energy from said at least one optical light source;
- wherein said optical sensor is in a fixed spatial relationship with said second coordinate system;
- wherein said optical sensor produces said second data signal representative of energy detected from said at least one optical light source.

20. The system of claim 19 wherein said coupling arrangement comprises:
- a optical subsystem light source in a fixed relationship with said first coordinate system;
- wherein said optical sensor is further configured to detect energy from said optical subsystem light source,
- wherein said optical sensor produces said coupling location signal representative of energy detected from said optical subsystem light source.

21. A system for determining the location of one or more objects, comprising:
- a first subsystem having a first set of sensors and a first coordinate system, said first set of sensors producing a first data signal indicative of the position and orientation of said one or more objects within said first coordinate system, wherein said first subsystem produces a first subsystem location signal, responsive to said first data signal, which is indicative of the location of said one or more objects within said first coordinate system, wherein said first data signal is also provided to a second subsystem;
- said second subsystem having a second set of sensors and a second coordinate system, said second set of sensors producing a second data signal indicative of the position and orientation of said one or more objects within said second coordinate system, wherein said second subsystem produces a second subsystem location signal, responsive to said second data signal, which is indicative of the location of said one or more objects within said second coordinate system, wherein said second data signal is also provided to said first subsystem;

a coupling arrangement for producing a coupling location signal indicative of the location of one of said first and second subsystems within the coordinate system of the other subsystem; and a processor responsive to said coupling location signal and at least one of said subsystem location signals for locating said one or more objects within said first coordinate system of said first subsystem;

wherein said first subsystem uses said second data signal to enhance the robustness and accuracy of said first subsystem location signal;

wherein said second subsystem uses said first data signal to enhance the robustness and accuracy of said second subsystem location signal.

* * * * *